United States Patent [19]

White

[11] Patent Number: 4,542,540

[45] Date of Patent: Sep. 24, 1985

[54] INTRAOCULAR LENS

[76] Inventor: Thomas C. White, 1127 Holly Dr., Sioux Falls, S. Dak. 55705

[21] Appl. No.: 502,312

[22] Filed: Jun. 8, 1983

[51] Int. Cl.$^4$ .......................... A61F 1/16; A61F 1/24
[52] U.S. Cl. ........................................................ 623/6
[58] Field of Search .............................................. 3/13

[56] References Cited

U.S. PATENT DOCUMENTS

| | | | |
|---|---|---|---|
| 4,092,749 | 6/1978 | Kelman | 3/13 |
| 4,159,546 | 7/1979 | Shearing | 3/13 |
| 4,174,543 | 11/1979 | Kelman | 3/13 |
| 4,242,760 | 1/1981 | Rainin | 3/13 |
| 4,244,060 | 1/1981 | Hoffer | 3/13 |
| 4,328,595 | 5/1982 | Sheets | 3/13 |
| 4,338,687 | 7/1982 | Rainin | 3/13 |
| 4,340,979 | 7/1982 | Kelman | 3/13 |
| 4,343,050 | 8/1982 | Kelman | 3/13 |
| 4,370,760 | 2/1983 | Kelman | 3/13 |
| 4,403,353 | 9/1983 | Tennant | 3/13 |
| 4,412,359 | 11/1983 | Myers | 3/13 |
| 4,418,431 | 12/1983 | Feaster | 3/13 |
| 4,435,855 | 3/1984 | Pannu | 3/13 |

FOREIGN PATENT DOCUMENTS 0053384 6/1982 European Pat. Off. .................. 3/13

OTHER PUBLICATIONS

American Medical Optics Model AC/PC-55 Anterior/Posterior Chamber (Pannu) Intraocular Lenses, fact sheets on lenses manufactured by American Medical Optics, (4 pages), Jan. 1982.
Americal IOL International Intraocular Lenses, advertisement for Americal IOL International, 15542 Graham St., Huntington Beach, CA 92647, USA, Style 115, Shepard Universal A/C IOL, "One-Size-Fits-All", Dec. 29, 1981.

Primary Examiner—Ronald L. Frinks
Attorney, Agent, or Firm—James R. Haller; Gregory P. Kaihoi

[57] ABSTRACT

An intraocular lens device is provided with fixation elements for centering it in the eye. At least one of the fixation elements comprises an elongated resilient strut carried at one end by the lens and having a first portion extending outwardly of the lens generally toward circumferential eye structure, the second portion having a contacting surface engageable with the eye structure, and a third portion extending from the contact surface generally inwardly toward the lens for a distance, measured radially inwardly toward the lens axis, of at least about two-fifths of the radial distance of the contact surface from the lens axis. The third portion has a free end, providing the at least one fixation element with substantial elastic flexibility. The generally inwardly-extending third portion of the strut prevents the end of the strut from becoming captured by a peripheral iridectomy opening.

12 Claims, 8 Drawing Figures

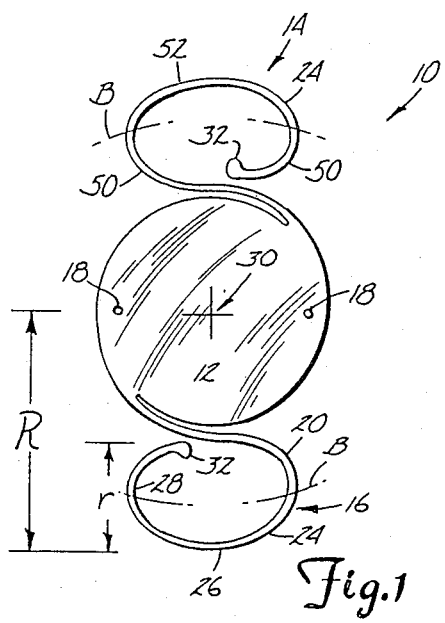
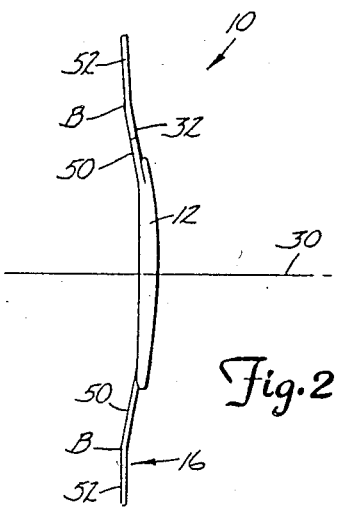
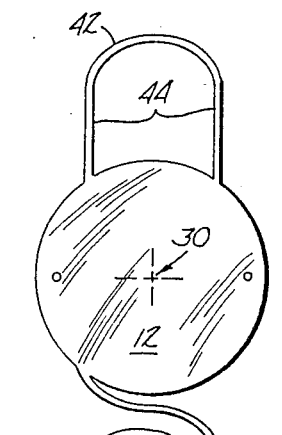
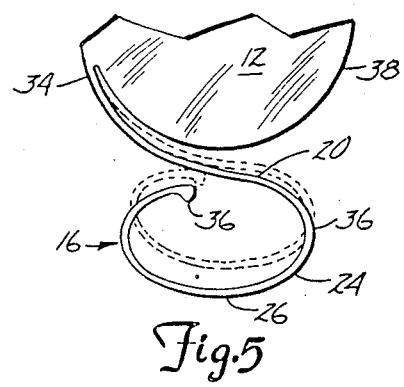
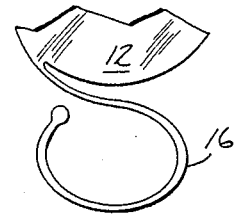

INTRAOCULAR LENS

TECHNICAL FIELD

This invention is in the field of medical prosthesis, and particularly relates to the use of artificial lenses to replace tissue lenses removed during cataract surgery.

BACKGROUND ART

Cataract surgery involves the removal of the lens or lens nucleus from the eye of a patient, and it is common in such procedures to implant within the eye an artificial intraocular lens, the lens being supported in either the anterior or posterior chambers and being supported by wires or other structure that extend from the lens outwardly into contact with supportive, circumferential grooves or other structure adjacent the iris.

Typical intraocular lenses are disclosed in the following references:
U.S. Pat. No. 4,092,743 (Kelman)
U.S. Pat. No. 4,174,543 (Kelman)
U.S. Pat. No. 4,261,065 (Tennant)
U.S. Pat. No. 4,328,595 (Sheets)
U.S. Pat. No. 4,338,687 (Rainin)
U.S. Pat. No. 4,340,979 (Kelman)
U.S. Pat. No. 4,343,050 (Kelman)
U.S. Pat. No. 4,370,760 (Kelman)

Intraocular lenses in general are characterized by including a central lens or lenticular portion, and two or more struts, usually radially resilient, that extend outwardly of the lens and which gently but elastically engage appropriate circumferential eye structure adjacent the iris. The struts of intraocular lenses that are to be employed in the anterior chamber of the eye commonly engage the internal scleral sulcus, commonly called the "angle", formed between the iris and the internal periphery of the cornea, avoiding substantial contact or interference with the trabacular meshwork. Intraocular lenses intended to be mounted in the posterior chamber commonly have struts or other fixation devices that engage the ciliary recess or the circumferential edges of the posterior lens capsule that remains after removal of the lens nucleus.

In normal human eyes, aqueous humor is discharged into the posterior chamber, flows through the pupil into the anterior chamber, and is removed from the anterior chamber by means of the trabacular meshwork and Schlemm's canals adjacent the internal scleral recess. When the flow of aqueous humor in this manner is restricted or blocked, as may occur when the anterior face of the vitreous humor comes forward into contact with the iris following cataract surgery, acute glaucoma can result. Accordingly, one or more small surgical iridectomies are routinely performed in the iris during cataract surgery to provide alternate flow paths for aqueous humor. Peripheral iridectomies preferably are basal, that is, they are formed at the periphery of the iris. Non-basal peripheral iridectomies, formed in the iris at positions spaced inwardly from its periphery, have also been used but are less preferred in that they can become blocked or plugged by the anterior vitreous face.

Intraocular lenses commonly are surgically oriented so that their supporting structure is rotated out of alignment with basal peripheral iridectomies, and it generally is expected that the rotational position of intraocular lenses will remain fixed permanently. Intraocular lenses commonly are formed with small holes or indentations adjacent the lens periphery to accept instruments enabling surgeons to rotate the lenses into desired positions spaced rotationally from openings formed through basal peripheral iridectomy procedures.

Unfortunately, intraocular lenses seldom remain permanently fixed against rotation with respect to the lens axis. The lenses may in fact be rotationally displaced through commonplace rubbing of the eyes, with the result that the lens fixation elements over a period of months or years may come into contact with and may actually enter basal peripheral iridectomies formed during cataract surgery. Inflammation of the iris (iritis) may result, but more importantly, the lens itself, due to the resulting loss of placement of its fixation elements, may tilt or may become dislocated with respect to the pupillary axis. The lens itself, if implanted in the anterior chamber, may touch and cause severe damage to the inner corneal surface, or, if placed in the posterior chamber, may cause rupture of the anterior vitreous face causing vitreous prolapse into the iridectomy wound, in turn leading to cystoid macular (retinal) edema. The undesired rotation of intraocular lenses in this manner, and the resulting problems that arise, have only recently been recognized. Unfortunately, such problems often arise months or years after a lens has been implanted and routine consultation with a surgeon has been terminated. As a result, severe damage to the eye can readily occur before corrective surgical steps can be taken.

Certain of the fixation elements previously employed with intraocular lenses are of wire or of a springy, wire-like material. The wire is formed into a "U"-shaped loop with the ends of the loop each being fixed to the lens. To the extent that the loops are smoothly curved, protrusion into or through an iridectomy opening may be avoided; however, the fixation of such loops at both ends to the lens reduces the elasticity of the loops. The lens with the semi-rigid fixation loops accordingly is difficult to insert and properly place within the eye since the loops are not highly elastic and are deformed only with some difficulty. It has been proposed in U.S. Pat. 4,338,687 to provide the lens itself with internal springs which resiliently receive ends of the "U"-shaped loops to enable the loops as a whole to be elastically moved toward and away from the lens periphery. This lens structure, however, is quite complicated and expensive. The increase in lens thickness required to accommodate the spring mechanism adds substantial weight to the device, resulting in increased potential damage to eye structures.

DISCLOSURE OF INVENTION

The present invention provides an intraocular lens having fixation elements carried by it for supportive engagement with eye structure circumferential of the pupillary axis. The invention is characterized on the one hand by including at least one fixation element which is springy and resilient to enable easy insertion and placement of the lens within an eye, but which on the other hand avoids structure likely to be captured by a peripheral iridectomy opening. At least one of the fixation elements comprises an elongated resilient strut carried at one end by the lens. The strut includes a first portion extending outwardly of the lens generally toward the circumferential eye structure, a second portion having a contact surface engageable with the circumferential eye structure, and a third portion extending from the contact surface inwardly toward the lens for a distance, measured radially inwardly toward the lens axis, of at least about two-fifths of the radial distance of the contact surface from the lens axis when the strut is at rest. The third portion has a free end providing the fixation element with substantial elasticity toward and away from the circumferential supporting structure of the eye.

Desirably, the first portion of the strut comprises a proximal portion carried by the lens and which spirals outwardly of the lens periphery in one direction, and a distal portion into which the proximal portion merges and which is curved in the opposite direction outwardly of the lens periphery, the latter merging into the contact portion. The free end of the third strut portion is either itself spaced from the lens axis by a distance not more than three-fifths of the radial distance of the contact surface from the lens axis, or is bounded by desirably gently curved portions of the fixation element; that is, the radius of curvature taken along the length of the strut of all outer tissue-confronting, outwardly facing surfaces of the strut extending outwardly of the lens axis more than three-fifths of the radial distance from the lens axis to the contact surface preferably is at least about 0.8 millimeters.

Movement of the contact surface of the fixation element toward or away from the lens axis results in movement of the free end of the element toward and away from the axis. The free end preferably is blunt or may be provided with a small knob.

Viewed in cross-section normal to the lens axis, the fixation elements desirably include inner portions extending from the lens at an angle to the plane of the lens and outer portions lying generally in a plane parallel to but spaced slightly from the plane of the lens. As a result, the lens structure, when implanted in the eye, carries the lens in a vaulted orientation spaced from the iris.

BRIEF DESCRIPTION OF DRAWINGS

FIG. 1 is a plan view of an intraocular lens device of the invention;

FIG. 2 is a side view of the device of FIG. 1;

FIG. 3 is a modified version of a device of the invention, shown in plan view;

FIG. 4 is a broken-away plan view of another modification of the device;

FIG. 5 is a broken-away view, in plan, showing the elastic movement of a fixation element;

BEST MODE FOR CARRYING OUT THE INVENTION

Figure 6:
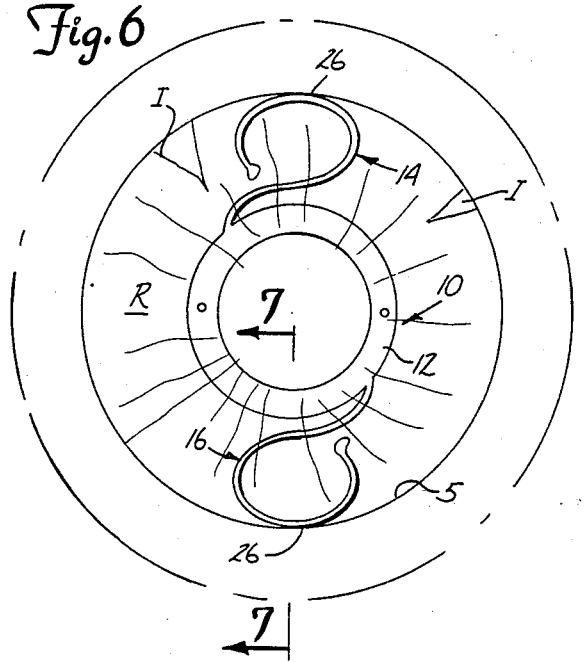
FIG. 6 is an anterior view of an eye showing implantation of the device of the invention in the anterior chamber.

Referring first to FIGS. 1 and 2, a preferred device of the invention is shown generally as (10) and includes a lens (12) and fixation elements (14), (16). The fixation elements in this preferred embodiment are identical and are two in number, although three or four or more elements, of similar or different shapes, may be utilized.

The lens (12) may be of any appropriate curvature, desirably plano-convex, and the lens and the fixation elements desirably are formed as one piece as by molding. Alternatively, the fixation elements may be attached to the lens after manufacture of the latter. The lens may include small sockets or openings (18) providing grasping points for an appropriate tool and enabling a surgeon to rotate the lens within the eye after the lens has been inserted.

The lenses and fixation elements may be of any appropriate material, but preferably are made of an optically clear plastic such as polymethylmethacrylate. Molding and/or lathe cutting of lenses are well known and need not be described in detail. If the fixation elements are attached to the lens after manufacture of the latter (as by inserting and adhesively bonding the elements within lens apertures formed desirably in or adjacent the lens periphery), the fixation elements may be of another plastic material, not necessarily transparent, such as polypropylene. The fixation elements (14), (16) are desirably gently curved, thin, resilient, wire-like struts and may have thicknesses on the order of about 0.25 mm. Strut (16) shown in FIG. 1 includes a first portion (20) that is attached to and is carried at one end (22) by the lens, preferably the lens periphery, and which extends outwardly of the lens generally toward the circumferential tissue of the eye by which the lens is to be supported. A second portion of the strut is designated (24) and includes a contact surface (26) that is engageable with the circumferential eye structure. A third portion of the strut, designated (28), extends thence inwardly generally toward the lens for a distance, measured radially toward the lens axis (30), of at least about two-fifths of the radial distance of the contact surface (26) from the lens axis (30) when the strut is in its relaxed or at rest position. The third portion has a free end (32).

The radial distance of the contact surface (26) from the lens axis (30) when the strut is in its rest position is designated in FIG. 1 as "R", and the distance, measured radially from the contact surface (26) toward the lens axis (30) through which the third portion (28) of the strut (16) extends is designated "r". The ratio r/R desirably is not less than about 0.40, and preferably is in the range of about 0.40 to about 0.50. The lens portion may have a diameter in the range of about 5–6 mm. and the at-rest diameter taken across the fixation elements may be in the range of about 12–14 mm.

Figure 7:
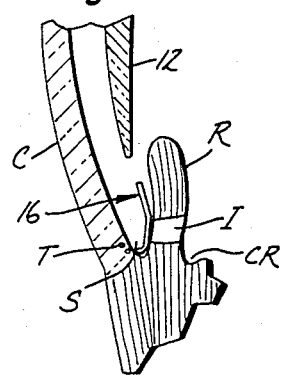
FIG. 7 is a broken-away, cross-sectional view taken along lines 7—7 of FIG. 6, with eye structure shown somewhat schematically.
Figure 8:
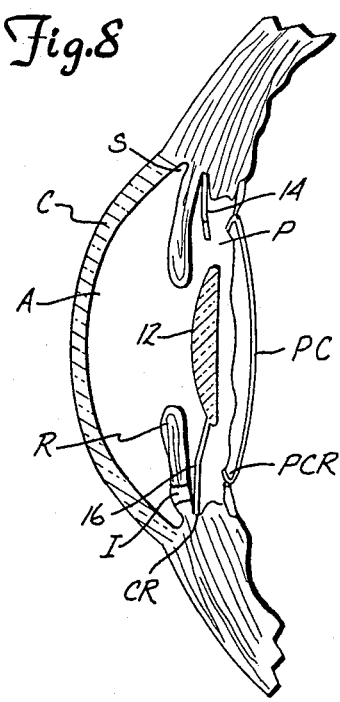
FIG. 8 is a cross-sectional view similar to FIG. 7 but showing the implantation of a lens device of the invention in the posterior chamber of the eye.

In a preferred embodiment, that portion of the strut structure (16) which is spaced radially from the lens axis (30) by at least three-fifths of the radial distance between the lens axis (30) and the contact surface (26) is formed with outwardly facing, tissue-confronting surfaces having radii of curvature taken along the length of the strut of at least about 0.8 millimeters, thereby avoiding the presence of sharp corners or edges within the zone within which may be found a peripheral iridectomy opening I (FIGS. 6–8).

The fixation elements typified by element (16) in FIG. 1, in accordance with this invention, are resiliently or elastically moveable inwardly and outwardly of the lens, as shown schematically in FIG. 5. Preferably the first portion (20) of the strut (referring to FIG. 5) comprises a proximal portion (34) and a distal portion (36), the latter smoothly joining the proximal portion to the second, circumferential eye structure-contacting portion (24). The proximal portion (34) desirably is smoothly curved and spirals generally outwardly of the lens periphery in one direction, as shown in FIG. 5, and the distal portion (36) is curved in the opposite direction outwardly of the lens periphery. The spirally curved portion (34), because of its gentle curvature in a direction diverging only gradually from the periphery (38) of the lens, is quite elastic. When a force is exerted on the contact surface (26) generally inwardly toward the lens axis, preferably a substantial amount of the resultant elastic movement of the strut is afforded by the proximal portion (34), the strut moving from its solid line rest position into the position shown in dashed lines in FIG. 5. When the force is removed, the strut returns resiliently toward the solid line relaxed or rest position shown in FIG. 5. It will be noted that the configuration of the strut distally of the proximal portion (34) does not change substantially under the application and removal of such force. The fixation element (16) hence is elastically moveable between its rest position shown in solid lines in FIG. 5 to a stressed position shown in phantom lines in FIG. 5, the latter position typifying the position of the strut when inserted in an eye for exertion of gentle pressure generally radially outwardly of the lens upon supportive circumferential eye structure. The dimensions and dimensional ratios provided herein refer to the fixation elements when in their rest position.

Referring again to FIG. 2, it will be observed that each strut (14), (16) is desirably bent at circumferential line "B" (shown in dashed lines in FIG. 1) to provide an inner portion (50) that extends at an angle to the plane of the lens and an outer portion (52) that includes the contact portion (24) and that lies generally in a plane parallel to but spaced slightly from the plane of the lens. In this manner, the lens (12) is spaced anteriorly or posteriorly of the iris R when the lens device is inserted in an eye, as shown best in FIGS. 7 and 8. Desirably, but not necessarily, the strut end (32) is positioned within the inner angled portion (50) so that the end (32) is generally between the planes of the lens and the outer portion (52) when the strut is in its installed, slightly radially compressed position.

Variations of the lens device of the invention are shown in FIGS. 3, 4 and 6. Similar numerals are employed to designate elements that are the same as or similar to those shown in FIGS. 1, 2 and 5.

The lens of FIG. 3 employs one fixation element (16) that is similar to that shown in FIG. 1, and another fixation element (40) in the shape of a "U"-shaped loop, the ends of the loop being carried by or attached to the periphery of the lens (12) and the fixation elements (16), (40) being diametrically opposed. The U-shaped loop (40) may have some radial resilience; its upper end (42) may be flattened somewhat upon the application of a radial force, and the legs (44) accordingly may be spread slightly. Primary resilience is afforded by the fixation element (16), however. Use of the intraocular lens shown in FIG. 3 generally requires that the diameter of the circumferential eye structure to be contacted by the fixation elements be measured with some exactness to assure that the axis (30) of the lens substantially coincides with the pupillary axis.

It will be understood that the length of the third portion (28) of the strut (16) may be extended somewhat in comparison to the configuration shown in FIG. 1. For example, the third portion (28) may be sufficiently extended as to position the strut end (32) substantially at but not in contact with the periphery of the lens. The third portion (28) may also be extended into a spiral configuration as typified in FIGS. 3 and 5. Although the end (32) of the strut (16) may be positioned adjacent the contact surface (26) as shown in FIG. 3, the strut (16) lies substantially in a single plane (slight bending of the plane is permitted) so that the terminus or end (32) is at least largely bounded and enclosed by the other smoothly curved portions of the strut that directly confront eye structure in the plane of the strut and is thus prevented from being captured in an iridectomy opening. The configuration shown in FIG. 4, in which the free end (32) is nearer the periphery of the lens and the configuration of the strut resembles a bass clef symbol, is preferred. Desirably, the radius of curvature measured along the length of the strut of all tissue-confronting, outwardly-facing surfaces of the strut that extend outwardly of the lens axis more than about three-fifths of the radial distance from the lens axis to the contact surface is at least about 0.8 mm.

In FIGS. 6, 7 and 8, the cornea of an eye is designated generally as "C", the anterior chamber as "A", the posterior chamber as "P", the iris as 37 R", the ciliary recess as "CR", the internal scleral sulcus (the "angle") as "S", and the posterior capsule of the capsular bag as "PC", the latter having a peripheral rim designated "PCR".

Following common surgical techniques, the anterior chamber is entered through an incision made through the cornea adjacent the limbus, and the natural lens or lens nucleus is removed, using common procedures. One or more peripheral iridectomies are then performed, leaving openings "I" that are generally triangular in shape and that extend inwardly toward the pupil from the periphery of the iris. I prefer to perform several such iridectomies, as shown in FIG. 6, to insure proper flow of aqueous humor from the posterior chamber to the anterior chamber.

A device of the invention, such as that shown in FIG. 6, is then inserted through the corneal incision. If the device is to be positioned in the anterior chamber, the struts (16) are positioned within the internal scleral sulcus as shown in FIG. 7, care being taken to avoid substantial contact or interference with the trabacular meshwork shown at "T" in FIG. 7. Only a very small amount of force is required to elastically compress the struts (16), and the size of the lens device (10) is chosen so that the surfaces (26) press outwardly gently against the internal scleral sulcus S. The surfaces (26) are gently curved so as to make more than point contact with the sulcus S, the desired contact extending across several millimeters measured circumferentially of the sulcus and thus preventing the lens from twisting or turning in the eye. When the lens is properly positioned and rotated so that the struts extend into contact with superior and inferior portions of the circumferential supportive eye tissue, the cornea is closed using common techniques. To space the struts rotationally from the iridectomy openings, the device may be rotated so that the struts extend medially and laterally from the lens. It will be understood that the lens (12) is vaulted anteriorly slightly from the internal scleral sulcus, the lens thus being spaced between the iris R and the inner surface of the cornea C. The lens is suspended in aqueous humor.

In the event that the lens device is to be positioned in the posterior chamber, as shown in FIG. 8, the pupil is dilated, if possible, and the device is passed through the pupil and is positioned with the contact surfaces of the struts (16) lying against and within the circumferential groove defining the ciliary recess CR, the lens (12) being vaulted posteriorly of the iris and being spaced posteriorly of the iris R and, desirably, anteriorly of the posterior lens capsule PC. If desired, the strut (16) may instead be supported within the rim PCR of the posterior lens capsule.

Referring again to FIG. 3, the surface (26) which is oriented to contact the circumferential eye structure to support the lens (12) in place may be provided with two or more outwardly extending projections or "feet" of which one is designated (27). The feet are intended to contact the circumferential eye structure at two or more spaced points to thus avoid contact with the circumferential structure over a wide area and to support the lens against tilting. Although such structure is included within the broader aspect of the invention, I prefer to form the surface (26) as a gently-rounded surface as shown in FIG. 1, thus providing line contact with the supporting circumferential eye structure. Although the contact surface (26) preferably is maintained generally out of contact with tissue involved in the transfer of aqueous humor, some interference with such tissue is readily tolerated.

While a preferred embodiment of the present invention has been described, it should be understood that various changes, adaptations and modifications may be made therein without departing from the spirit of the invention and the scope of the appended claims.

What is claimed is:

1. An intraocular lens device comprising a
lens for placement adjacent a side of the iris of an eye with the lens axis substantially aligned with the pupillary axis;
fixation elements carried by the lens for supportive engagement with eye structure circumferential of the pupillary axis, at least one fixation element comprising an elongated resilient strut carried at one end by the lens, the strut having a first portion extending outwardly of the lens generally toward said circumferential eye structure, a second portion having a contact surface engageable with the circumferential eye structure, and a third portion extending from the contact surface inwardly toward the lens for a distance, measured radially from the contact surface inwardly toward the lens axis and when the strut is at rest, of at least about two-fifths of the radial distance of the contact surface from the lens axis, said third portion having a free end.

2. The lens device of claim 1 wherein the first
portion of the strut comprises a proximal portion carried by the lens and spiraling outwardly of the lens periphery in one direction, and a distal portion curved in the opposite direction outwardly of the lens periphery, the latter merging into the proximal portion.

3. The intraocular lens device of claim 1
wherein the free end of said third strut portion is spaced from the contact surface by at least about two-fifths of the radial distance of the contact surface from the lens axis.

4. The intraocular lens device of claim 1
wherein the radius of curvature taken along the length of the strut of all outer, tissue-confronting outwardly-facing surfaces of the strut extending outwardly of the lens axis more than about three-fifths of the radial distance from the lens axis to the contact surface is at least about 0.8 millimeters.

5. The intraocular lens device of claim 1
wherein said free strut end is closely adjacent but not in contact with the periphery of the lens.

6. The intraocular lens device of claim 1
wherein the free strut end is bounded, in the direction of the contact surface, by said second strut portion.

7. The intraocular lens device of claim 1 in
which the second and third portions of the strut are configured in the form of a bass clef symbol.

8. The intraocular lens device of claim 1 wherein the third portion of the strut extends toward the lens from the contact surface a distance of between 0.40 and 0.5 of the radial distance from the contact surface to the lens axis.

9. An intraocular lens device comprising a lens
for placement adjacent a side of the iris of an eye with the lens axis substantially aligned with the pupilary axis; fixation elements carried by the lens for supportive engagement with eye structure circumferential of the pupilary axis, at least one fixation element comprising an elongated, resilient strut carried at one end by the lens, the strut having a first portion extending outwardly of the lens generally toward said circumferential eye structure, a second portion having a contact surface engageable with the circumferential eye structure, and a third portion extending from the contact surface inwardly toward the lens axis for a distance, measured radially inwardly toward the lens axis and when the strut is at rest, of from about two-fifths to about one-half of the radial distance of the contact surface from the lens axis, said third portion having a free end, the radius of curvature of all outwardly facing surfaces of the strut extending outwardly of the lens more than about two-fifths of the radial distance from the lens axis to the contact surface being at least about 0.8 millimeters.

10. An intraocular lens device comprising a lens for placement adjacent a side of the iris of an eye with the lens axis substantially aligned with the pupillary axis; and
fixation elements carried by the lens for supportive engagement with eye structure circumferential of the pupillary axis, at least one fixation element comprising an elongated resilient strut carried at one end by the lens, the strut having a first portion extending outwardly of the lens generally toward said circumferential eye structure, said first portion including a proximal portion carried by the lens and spiraling outwardly of the lens periphery in one direction, and a distal portion curved in the opposite direction outwardly of the lens periphery, the latter merging into the proximal portion; a second portion having a contact surface engageable with the circumferential eye structure; and a third portion extending from the contact surface inwardly toward the lens for a distance, measured radially from the contact surface inwardly toward the lens axis and when the strut is at rest, of at least 0.40 of the radial distance of the contact surface from the lens axis, said third portion having a free end.

11. The intraocular lens device of claim 10 wherein the radius of curvature taken along the length of the strut of all outer, tissue confronting outwardly-facing surfaces of the strut extending outwardly of the lens axis more than about three-fifths of the radial distance from the lens axis to the contact surface is at least about 0.8 mm.

12. An intraocular lens device comprising:

a lens for placement adjacent a side of the iris of an eye with the lens axis substantially aligned with the pupillary axis; and fixation elements carried by the lens for supportive engagement with eye structures circumferential of the pupillary axis, at least one fixation element comprising an elongated resilient strut carried at one end by the lens, the strut having:

a first portion extending outwardly of the lens generally towards said circumferential eye structure, said first portion including a proximal portion carried by the lens and spiraling outwardly of the lens periphery in one direction, and a distal portion curved in the opposite direction outwardly of the lens periphery, the latter merging into the proximal portion;

a second portion having a contact surface engageable with the circumferential eye structure; and a third portion extending from the contact surface inwardly toward the lens for a distance, measured radially from the contact surface inwardly toward the lens axis and when the strut is at rest, of between 0.40 and 0.50 of the radial distance from the contact surface to the lens axis, said third portion having a free end;

the radius of curvature taken along the length of the strut of all outer, tissue confronting outwardly facing surfaces of the strut extending outwardly of the lens axis more than about three-fifths of the radial distance from the lens axis to the contact surface being at least about 0.8 mm.

* * * * *